(12) United States Patent
Rhee et al.

(10) Patent No.: US 8,262,279 B2
(45) Date of Patent: Sep. 11, 2012

(54) AUTOMATED RECIRCULATION SYSTEM FOR LARGE PARTICLE SIZE ANALYSIS

(75) Inventors: Chulwoo Rhee, Daejeon (KR); Jaehwa Jin, Daejeon (KR); Minjun Kim, Daejeon (KR); Yikyun Kwon, Daejeon (KR)

(73) Assignee: Korea Institute of Geoscience and Mineral Resouces, Daejeon (KR)

( * ) Notice: Subject to any disclaimer, the term of this patent is extended or adjusted under 35 U.S.C. 154(b) by 900 days.

(21) Appl. No.: 12/149,694

(22) Filed: May 7, 2008

(65) Prior Publication Data
US 2008/0285377 A1 Nov. 20, 2008

(30) Foreign Application Priority Data
May 8, 2007 (KR) .......................... 10-2007-004407

(51) Int. Cl.
*B01F 15/02* (2006.01)
*B01F 15/00* (2006.01)
*B01F 7/00* (2006.01)
*E03B 7/07* (2006.01)

(52) U.S. Cl. ........ 366/132; 366/131; 366/133; 366/134; 366/135; 366/136; 366/137; 366/167.1; 366/168.1; 366/173.1; 366/307; 366/168.2; 366/174.1; 366/175.2; 137/563

(58) Field of Classification Search .......... 366/131–137, 366/167.1, 168.1, 173.1, 307, 563, 168.2, 366/174.1, 175.2; 137/563
See application file for complete search history.

(56) References Cited

U.S. PATENT DOCUMENTS

| 5,393,502 | A | * | 2/1995 | Miller et al. | ................. 422/261 |
| 6,394,642 | B2 | | 5/2002 | Tromley | |
| 6,491,421 | B2 | * | 12/2002 | Rondeau et al. | ................. 366/8 |
| 6,508,583 | B1 | * | 1/2003 | Shankwitz et al. | ........... 366/196 |

FOREIGN PATENT DOCUMENTS

| JP | 2-36333 | | 2/1990 |
| JP | 11-44629 | | 2/1999 |
| JP | 11-044629 | * | 2/1999 |
| JP | 2006-133103 | | 5/2006 |

* cited by examiner

*Primary Examiner* — Christopher Schatz
*Assistant Examiner* — Matthew Hoover
(74) *Attorney, Agent, or Firm* — Clark & Brody

(57) ABSTRACT

The present invention relates to a wet-type recirculation system for particle size analysis of sample including coarse particles (hundreds to thousands μm). According to the wet-type recirculation system of the present invention, the mixture liquid is recirculated using not a single recirculation line but two recirculation lines between the mixer and the particle size analyzer and the recirculation lines are connected with the mixer at the upper inputting part side of the mixer to discharge the mixture liquid. Further, the rotatable baffle is attached to the inside of the mixer to generate vortex in a horizontal direction as well as a vertical direction within the reservoir of the mixer and the baffle is rotated by a pressure of the mixture liquid discharged from the two recirculation lines to form vortex. Consequently, the mixture liquid in which fine particles and coarse particles are uniformly mixed is provided to the particle size analyzer and thus reliable and accurate result of the particle size distribution measurement can be obtained when particle size measurement of sediment including from fine particles of several μm to coarse particles of thousands μm.

5 Claims, 6 Drawing Sheets

AUTOMATED RECIRCULATION SYSTEM FOR LARGE PARTICLE SIZE ANALYSIS

TECHNICAL FIELD

The present invention relates to an automated recirculation system for particle size analysis of sample including coarse particles (hundreds to thousands μm).

BACKGROUND ART

A particle size of sediment is a basic physical parameter which has an influence on entrapment, transportation and deposition by sediment transportation medium. Therefore, the particle size of the sediment is basic data which allows an analogy to the origin, transportation path and deposition condition of the sediment.

The particle size which is generally referred in a sedimentology is measured directly using a caliper in a case of gravel, through a dry and wet sieving in a case of sand, and using a difference in deposition speeds based on the Stoke's law in a case of fine sediment having a particle size of less than the size of silt (less than 63 μm).

Therefore, in actual samples, the particle size is mostly measured using at least two methods. Since the measuring method is varied as a particle class, the particle size actually represented by the method may include a maximum caliper diameter, a sieve diameter and a diameter of a quartz ball which is hydraulically equal.

That is to say, in a particle size analysis of geological sediment, the problem is a statistical processing of heterogeneous measured values as well as ambiguities and disagreements in the physical properties represented by the measured value which is a fundamental problem.

Therefore, a result of the particle size analysis which is expressed by percent by weight or percent by volume of particles in each class could be statistically processed and interpreted more coherently than the present if the measuring method is identical irrespective of the class.

Since most sediment is composed of sand and mud, if a satisfactory result is obtained by a method capable of measuring simultaneously the particle sizes of the sand and the mud, it would be possible not only to reduce the ambiguities in the particle size analysis for the sediment but also to reduce time and efforts taken into a particle size measuring process according to the deposition method.

In a case of sandy sediment, it is possible to separate particles having a diameter of more than 63 μm (4Φ) by the dry and wet sieving, but it is inefficient to separate particles having a diameter of less than 125 μm (3Φ) for a dry sample.

In a case of muddy sediment, in order to utilize a pipette method according to the Stoke's law, it is necessary to satisfy a rigid condition that the particles having a diameter of at least less than 50 μm (silt) should be dispersed to less than 1%.

Besides this principal restriction factor, there is a problem that much time and efforts are taken for a pre-process such as removal of organic substances and a post process such as drying and weighing of the sample in order to employ these methods.

Therefore, it has been a long desire of the researchers to develop a particle size analyzer which can eliminate an error according to an experimenter and easily complete a particle size analysis of the sample by measuring the particle size of the sandy and muddy sediments at a time through a minimum preprocess.

In a measurement of a particle size of the sediment including from fine particles of several μm to coarse particles of thousands μm, the most important challenge for obtaining a reliable result in the particle size analysis is to prevent the coarse particles from being sunken by the gravity and to obtain uniform mixing of the particles.

General wet-type particle size analyzer is mostly for particle size analysis of fine particles, and thus the mixing of the sample is conventionally carried out by microwave vibration of a mixing reservoir within the particle size analyzer and recirculation which is limited to an inside of the particle size analyzer. This mixing method is efficient for the particles having a fine size (several μm), but it is impossible to obtain the uniform mixing in the case of coarse particles.

When the sample mixing part is separated from the wet-type particle size analyzer and a mixture liquid is supplied to the particle size analyzer by a recirculation system, it is possible to measure more coarse particles. However, such analyzer also has a limitation that a uniform mixture liquid cannot supplied to the particle size analyzer in the case that a large amount of the coarse particles is included since there has been almost no study for an analyzer which measures all ranges of particle size.

DISCLOSURE OF THE INVENTION

It is an object of the present invention to provide an automated recirculation system for a wet-type particle size analyzer, in which a path for recirculating sample (mixture liquid) is added, a direction of the sample (mixture liquid) discharged to a mixing reservoir is controlled and a rotatable baffle is formed within the mixing reservoir, and thus a mixture liquid having uniformly mixed particles is supplied to a particle size analyzer even in a case of sediment including a large amount of coarse particles having a size of more than hundreds μm, thereby enhancing reliability and accuracy of a particle size analysis for the sample including the coarse particles.

The recirculation system for wet-type particle size analyzer according to the present invention is an apparatus for supplying a mixture liquid of sample and liquid (dispersing liquid) to a wet-type particle size analyzer 160, and is characterized in that a liquid supply pump 130 for supplying liquid from a liquid supply tank 110 to a mixer 210 is provided, a discharge port 213 connected with a side of a recirculation pump 150 and discharging a mixture liquid mixed with particles in the mixer 210 is provided, a pipe line connected with the other side of the recirculation pump 150 is branched and coupled to a liquid supply line L30 connected to the supply pump 130, a recirculation line L40 for discharging the mixture liquid to the mixer 210, a first analysis line L50 connected with a side of a particle size analyzer 160 and a discharge line L60 for discharging the mixture liquid to an outside of the recirculation system, and at least one rotatable baffle 211, 212 is attached to the mixer 210.

DETAILED DESCRIPTION OF MAIN ELEMENTS

Figure 1:
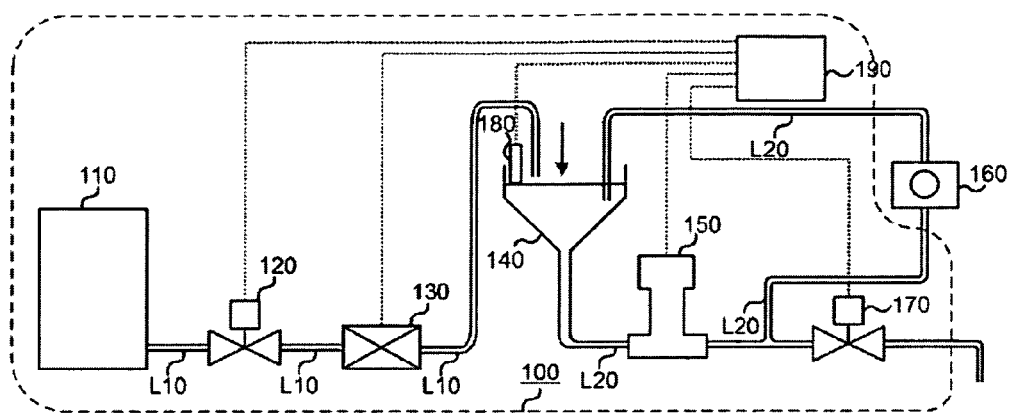
FIG. 1 is a schematic diagram of conventional wet-type recirculation system and particle size analyzer.

100: conventional wet-type sample mixer
110: liquid tank
120: liquid supply valve 130: liquid supply pump
140, 210: mixer 150: recirculation pump
160: particle size analyzer 170: drain valve
180: level sensor 211, 212: baffle

BEST MODE FOR CARRYING OUT THE INVENTION

Practical and presently preferred embodiments of the present invention are illustrative as shown in the following Examples and Comparative Examples.

However, it will be appreciated that those skilled in the art, on consideration of this disclosure, may make modifications and improvements within the spirit and scope of the present invention.

In order to describe the present invention more clearly, a conventional recirculation system 100 for supplying a mixture liquid to a wet-type particle size analyzer 160 is shown in FIG. 1.

In the conventional recirculation system 100 for a wet-type particle size analyzer, an upstream side end part of a recirculation line L20 is connected to a bottom part of a mixer 140 for mixing the sample and liquid (dispersing liquid) and generating the mixture liquid, a recirculating pump 150 is install on the recirculation line L20 and a drain valve 170 and the particle size analyzer 160 are connected to a downstream side end part of the recirculating pump 150. A downstream of the particle size analyzer 160 is connected to the recirculation line L20 to discharge the mixture liquid to an upper inputting part side (an arrow in FIG. 1) of the mixer 140.

Also, the liquid is supplied to the mixer 140 through a liquid supply line L10. The liquid contained in a liquid tank 110 is connected to the liquid supply line L10 and a liquid supply valve 120 and a liquid supply pump 130 are connected to the liquid supply line L10 and thus the liquid is discharged from a downstream of the liquid supply pump 130 through the liquid supply line L10 to the upper inputting part side of the mixer 140.

Generally, a level sensor 180 for controlling a level of the liquid is attached to the mixer 140. The level sensor 180, the recirculation pump 150, the liquid supply pump 130 and the liquid supply valve 120 are electrically connected with a control part 190 and thus their operations are controlled by a signal from the control part.

In the conventional recirculation system 100 as shown in FIG. 1, the mixture liquid is supplied and recirculated through the recirculation line L20 to the particle size analyzer 160 and a uniform mixing of the sample and the liquid is led by tapering a shape of a reservoir of the mixer 140, forming an impeller at a lower part of the mixer 140 (Japanese Patent Application Laid Open No. 2006-133103), or discharging the recirculated mixture liquid not to the upper inputting part but to both side surfaces thereof (U.S. Pat. No. 6,394,642), but there is a limitation that it is impossible to supply the mixture liquid having uniformly mixed particles to the particle size analyzer in the case of the sediment including a large amount of coarse particles having a size of more than hundreds μm.

The present invention is essentially characterized in that not a single recirculation line but two recirculation lines are used between the mixer 140 and the particle size analyzer 160 to recirculate the mixture liquid and the two recirculation lines are connected to the upper inputting part side of the mixer 140 to discharge the mixture liquid, and a rotatable baffle is attached to the inside of the mixer 140, the baffle being rotated by pressure of the mixture liquid discharged from the two recirculation lines to form vortex thereby obtaining the mixture liquid in which the sample including coarse particles is uniformly mixed.

Hereafter, a recirculation system for a particle size analyzer according to the present invention is described in more detail with reference to the attached figures. The same components are indicated by the same reference symbol for the clarification and the shape and size of the components may be magnified in the figures for easy comprehension.

Figure 2:
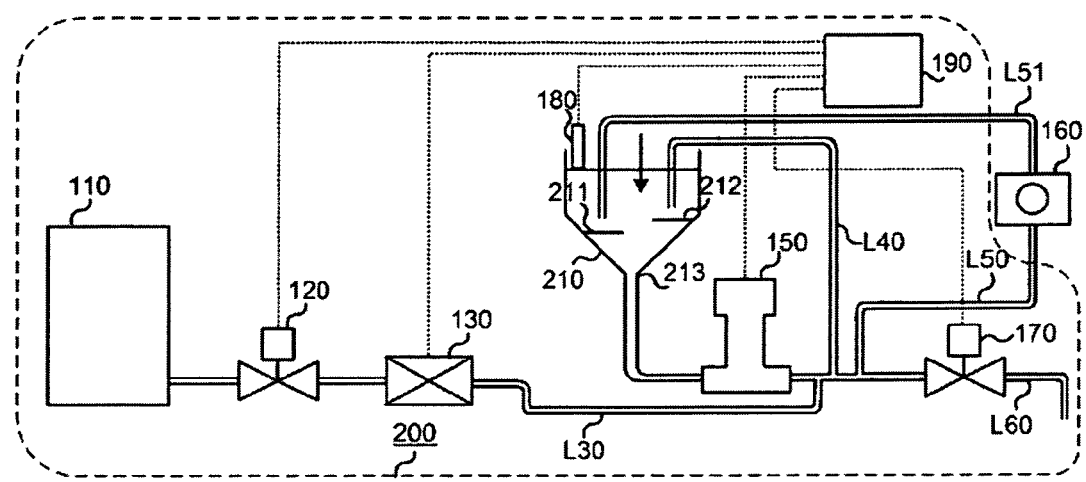
FIG. 2 is schematic diagram of a wet-type recirculation system according to the present invention.

A structure of a recirculation system 200 for measuring a coarse particle size distribution according to the present invention is shown in FIG. 2.

The recirculation system 200 for wet-type particle size analyzer according to the present invention is an apparatus for supplying a mixture liquid of sample and liquid (dispersing liquid) to a wet-type particle size analyzer 160, and is characterized in that a liquid supply pump 130 for supplying liquid from a liquid supply tank 110 to a mixer 210 is provided, a discharge port 213 connected with a side of a recirculation pump 150 and discharging a mixture liquid mixed with particles in the mixer 210 is provided, a pipe line connected with the other side of the recirculation pump 150 is branched and coupled to a liquid supply line L30 connected to the supply pump 130, a recirculation line L40 for discharging the mixture liquid to the mixer 210, a first analysis line L50 connected with a side of a particle size analyzer 160 and a discharge line L60 for discharging the mixture liquid to an outside of the recirculation system, and at least one rotatable baffle 211, 212 is attached to the mixer 210.

Also, likewise in FIG. 1, a level sensor 180 for controlling a level of the liquid is generally attached to the mixer 210. The level sensor 180, the recirculation pump 150, the liquid supply pump 130 and the liquid supply valve 120 are electrically connected with a control part 190 and thus their operations are controlled by a signal from the control part 190.

In the recirculation system 200 for wet-type particle size distribution measurement according to the present invention, a second analysis line L51 connected to the other side of the particle size analyzer 160 [190->160] and discharging the mixture liquid to the mixer 210, and the recirculation line L40 discharge the mixture liquid to an upper inputting part side (indicated by an arrow in FIG. 2) of the mixer 210. Therefore, as shown in FIG. 3, a further recirculation path B for the purpose of only recirculation of the particles mixing the particles by forming the vortex in the mixer 210 is formed besides a recirculation path A which is the same as the prior art.

Figure 4:
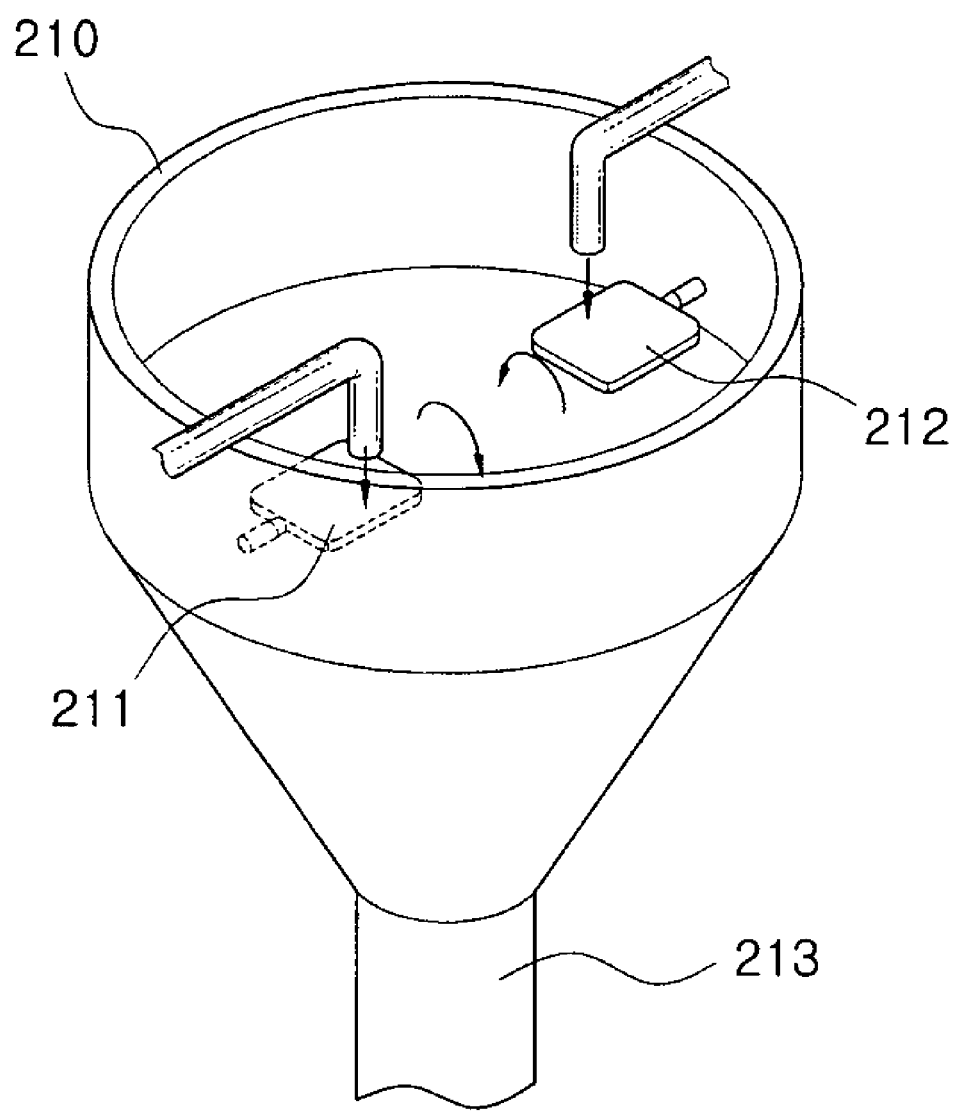
FIG. 4 is a perspective view of a mixer of the wet-type recirculation system according to the present invention.

Further, as shown in FIG. 4, the at least one baffle 211, 212 is rotated by a flow velocity of the mixture liquid discharged from the recirculation line L40 and the second analysis line L51, which form the two recirculation paths A and B, to the upper inputting part side of the mixer 210. Therefore, the more coarse particles are included in the sample, the faster the rotation of the baffle becomes and the larger the vortex in the mixer 210 becomes.

The baffle 211, 212 attached to a reservoir surface of the mixer 210 includes preferably a rectangular baffle plate and a baffle rotation shaft attached to the baffle plate. Also, it is preferable that the rectangular baffle has an area of 10 to 40% of a sectional area of the mixer 210 at a portion where the baffle is attached to the mixer 210.

Figure 3:
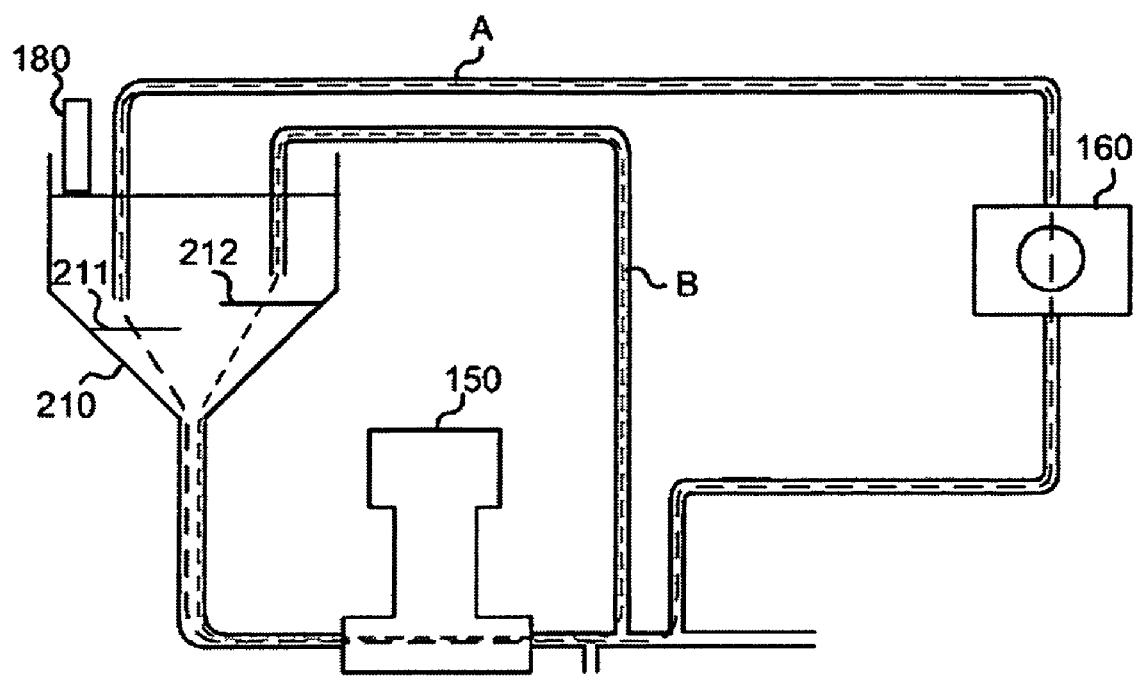
FIG. 3 is a schematic diagram of recirculation paths of the wet-type recirculation system according to the present invention.

At this time, when at least two baffles are attached to the reservoir surface of the mixer 210, it is more efficient in an aspect of vortex formation that the baffles are attached at the different heights from each other from the discharge port 213 of the mixer 210, as shown in FIGS. 2 and 3.

Figure 5:
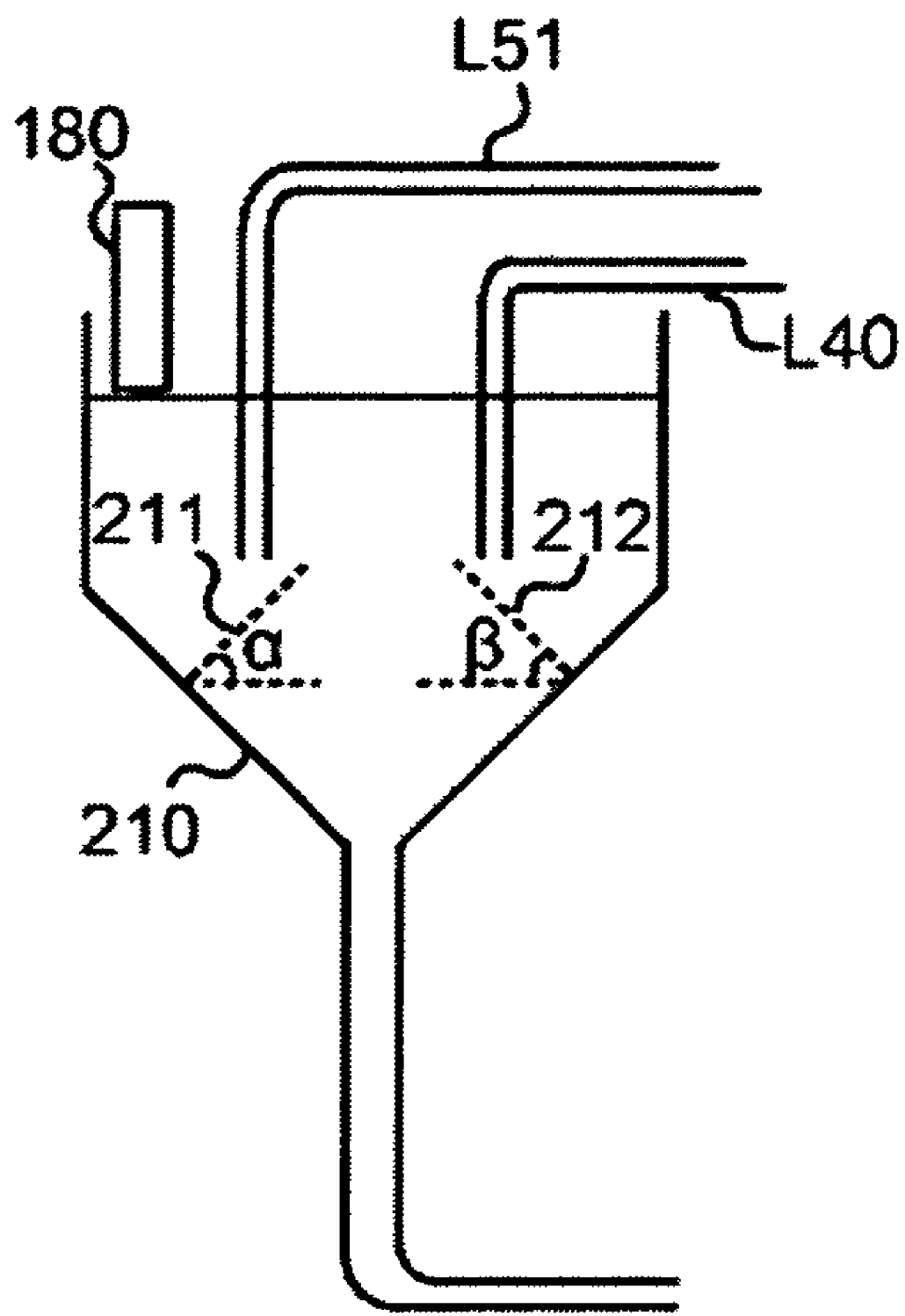
FIG. 5 is a schematic sectional view of the mixer of the wet-type recirculation system according to the present invention.

As shown in FIG. 5, the baffle may be attached to the reservoir surface of the mixer 210 with an angle of less than 90 degrees with respect to the reservoir surface or more than 0 degree with respect to the ground and preferably attached with an angle of less than 90 degrees with respect to the reservoir surface where the baffle is attached to the mixer 210 or more than 30 degrees with respect to the ground.

Also, the rectangular baffle plate may be formed with holes having a size enough to allow the particle or a group of particles of the sample to pass through.

As describe above, the at least two baffle is rotated by a flow velocity of the mixture liquid discharged from the recirculation line L40 and the second analysis line L51 to the upper inputting part side of the mixer 210. At this time, it is preferable to adjust the positions of the recirculation line L40 and the second analysis line L51 at the upper part of the mixer 210 to rotate the baffles in different directions from each other.

Figure 6:
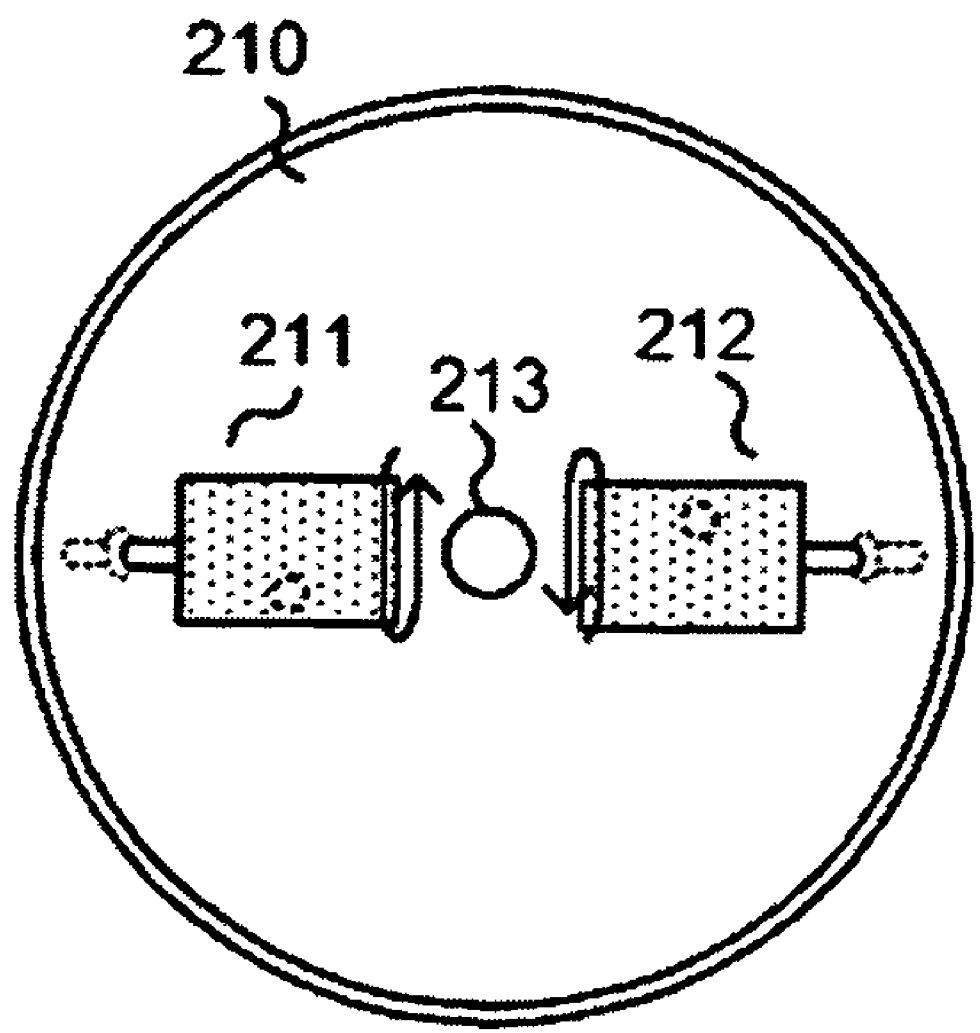
FIG. 6 is a schematic plan view of the mixer of the wet-type recirculation system according to the present invention.

For example, as shown in FIG. 6, when two rotatable baffles are attached to the reservoir surface of the mixer 210, one baffle 212 is rotated by the flow velocity of the mixture liquid discharged from the recirculation line L40 and the other baffle 211 is rotated by the flow velocity of the mixture liquid discharged from the second analysis line L51 and the two baffles 212 and 211 are rotated in the opposite directions to each other. Circles drawn by a dotted line on the baffle plates in FIG. 6 indicate center points where the mixture liquid discharged from the recirculation line L40 and the second analysis line L51 meets the baffle plates. Arrows FIG. 6 in indicate the rotation directions of the baffle plates 211 and 212 by the flow velocity of the mixture liquid and a force due to mass of the sample particles.

Therefore, in the wet-type recirculation system 200 according to the present invention, the mixture liquid is recirculated using not a single recirculation line but two recirculation lines A and B between the mixer 210 and the particle size analyzer 160 and the recirculation lines are connected with the mixer 210 at the upper inputting part side of the mixer 210 to discharge the mixture liquid. Further, the rotatable baffle is attached to the inside of the mixer 210 to generate vortex in a horizontal direction as well as a vertical direction within the reservoir of the mixer and the baffle is rotated by a pressure of the mixture liquid discharged from the two recirculation lines to form vortex. Consequently, the mixture liquid in which the sample including coarse particles is uniformly mixed is provided to the particle size analyzer 160 and thus reliability and accuracy of the particle size distribution measurement of the sample including the coarse particles is enhanced.

INDUSTRIAL APPLICABILITY

According to the wet-type recirculation system of the present invention, since mixture liquid is recirculated using two recirculation lines A and B and rotatable baffle forming vortex in horizontal and vertical directions is attached to a reservoir surface of the mixer, the mixture liquid in which fine particles and coarse particles are uniformly mixed is provided to the particle size analyzer and thus reliable and accurate result of the particle size distribution measurement can be obtained when particle size measurement of sediment including from fine particles of several μm to coarse particles of thousands μm.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A recirculation system for coarse particle size analysis in a wet-type particle size analyzer, in which a liquid supply pump for supplying liquid from a liquid supply tank to a mixer is provided,
  a discharge port connected with a side of a recirculation pump and discharging a mixture liquid mixed with particles in the mixer is provided,
  a pipe line connected with the other side of the recirculation pump is branched and coupled to a liquid supply line connected to the supply pump, a recirculation line for discharging the mixture liquid to the mixer, a first analysis line connected with a side of a particle size analyzer and a discharge line for discharging the mixture liquid to an outside of the recirculation system, and
  a second analysis line connected with another side of the particle size analyzer and discharging from the particle size analyzer to the mixer,
  the recirculation line and the second analysis line discharging the mixture liquid to an upper inputting part,
  wherein two rotatable baffles are attached to both side walls of the mixer, one baffle is rotated by a flow velocity of the mixture discharged from the recirculation line and the other baffle is rotated by a flow velocity of the mixture discharged from the second analysis line, and rotation directions of the two baffles are opposite each other.

2. The recirculation system for coarse particle size analysis as set forth in claim 1, wherein the baffle is attached to a reservoir surface of the mixer with an angle of less than 90 degrees with respect to the reservoir surface or more than 0 degree with respect to the ground.

3. The recirculation system for coarse particle size analysis as set forth in claim 1, wherein the baffle includes a rectangular baffle plate and a rotatable baffle rotation shaft attached to the baffle plate.

4. The recirculation system for coarse particle size analysis as set forth in claim 3, wherein the rectangular baffle has an area of 10 to 40% of a sectional area of the mixer at a portion where the baffle is attached to the mixer.

5. The recirculation system for coarse particle size analysis as set forth in claim 1, wherein the two baffles are attached at different heights from each other from the discharge port of the mixer.

* * * * *